US007068300B2

(12) United States Patent
Watai et al.

(10) Patent No.: US 7,068,300 B2
(45) Date of Patent: Jun. 27, 2006

(54) ENDOSCOPE IMAGE FILING SYSTEM AND ENDOSCOPE IMAGE FILING METHOD

(75) Inventors: Makoto Watai, Northport, NY (US); Hiroyuki Shibata, Yokohama (JP)

(73) Assignee: Olympus Corporation, Tokyo (JP)

( * ) Notice: Subject to any disclaimer, the term of this patent is extended or adjusted under 35 U.S.C. 154(b) by 684 days.

(21) Appl. No.: 10/224,603

(22) Filed: Aug. 20, 2002

(65) Prior Publication Data

US 2003/0043265 A1 Mar. 6, 2003

(30) Foreign Application Priority Data

Aug. 28, 2001 (JP) ............................. 2001-258469

(51) Int. Cl.
*H04N 7/18* (2006.01)
(52) U.S. Cl. ........................................ 348/74; 600/407
(58) Field of Classification Search ................. 348/74, 348/75, 14.09, 72; 358/296, 403; 707/104.1; 600/407; 386/46, 109, 125
See application file for complete search history.

(56) References Cited

U.S. PATENT DOCUMENTS

| 5,029,016 | A | | 7/1991 | Hiyama et al. | |
| 5,111,306 | A | * | 5/1992 | Kanno et al. | 358/403 |
| 5,187,579 | A | | 2/1993 | Hiyama | |
| 5,568,271 | A | * | 10/1996 | Fukuchi et al. | 386/46 |
| 5,659,741 | A | | 8/1997 | Eberhardt | |
| 5,697,885 | A | | 12/1997 | Konomura et al. | |
| 5,740,801 | A | * | 4/1998 | Branson | 600/407 |
| 5,872,527 | A | | 2/1999 | Yanagisawa | |
| 5,924,074 | A | | 7/1999 | Evans | |
| 6,269,379 | B1 | * | 7/2001 | Hiyama et al. | 707/104.1 |
| 6,356,295 | B1 | * | 3/2002 | Mano | 348/14.09 |
| 6,609,135 | B1 | * | 8/2003 | Omori et al. | 707/104.1 |

OTHER PUBLICATIONS

L. Kleinholz et al., "Multimedia and PACS- Setting the Platform for Improved and New Medical Services in Hospitals and Regions", Computer Assisted Radiology (1996) pp. 313-322.

* cited by examiner

*Primary Examiner*—Gims Philippe
(74) *Attorney, Agent, or Firm*—Scully, Scott, Murphy & Presser, P.C

(57) ABSTRACT

A personal computer is a main part of an image filing device. In accordance with a release trigger generated by pressing a release switch included in an electronic endoscope, the personal computer records image signals output from an endoscope device, which are associated with examination information relating to endoscope examination input through a keyboard and/or a mouse. Then, the personal computer displays image signals and/or information output from the endoscope device on a monitor. The personal computer searches and displays examination information in accordance with a search condition input by the keyboard and/or the mouse. In addition, the personal computer searches and displays examination information by changing a search range under a predetermined condition with respect to the search condition.

21 Claims, 10 Drawing Sheets

Last Name

[           44a           ]    [OK] [Cancel]
                                  44b

Patient / Exam

○ Non   ○ OK     [OK] [Cancel]
     45a          45b

Billing

○ Non
○ Selected Chanded
○ Selected Codes
○ Selected No Codes

46a

[OK] [Cancel]
 46b

46

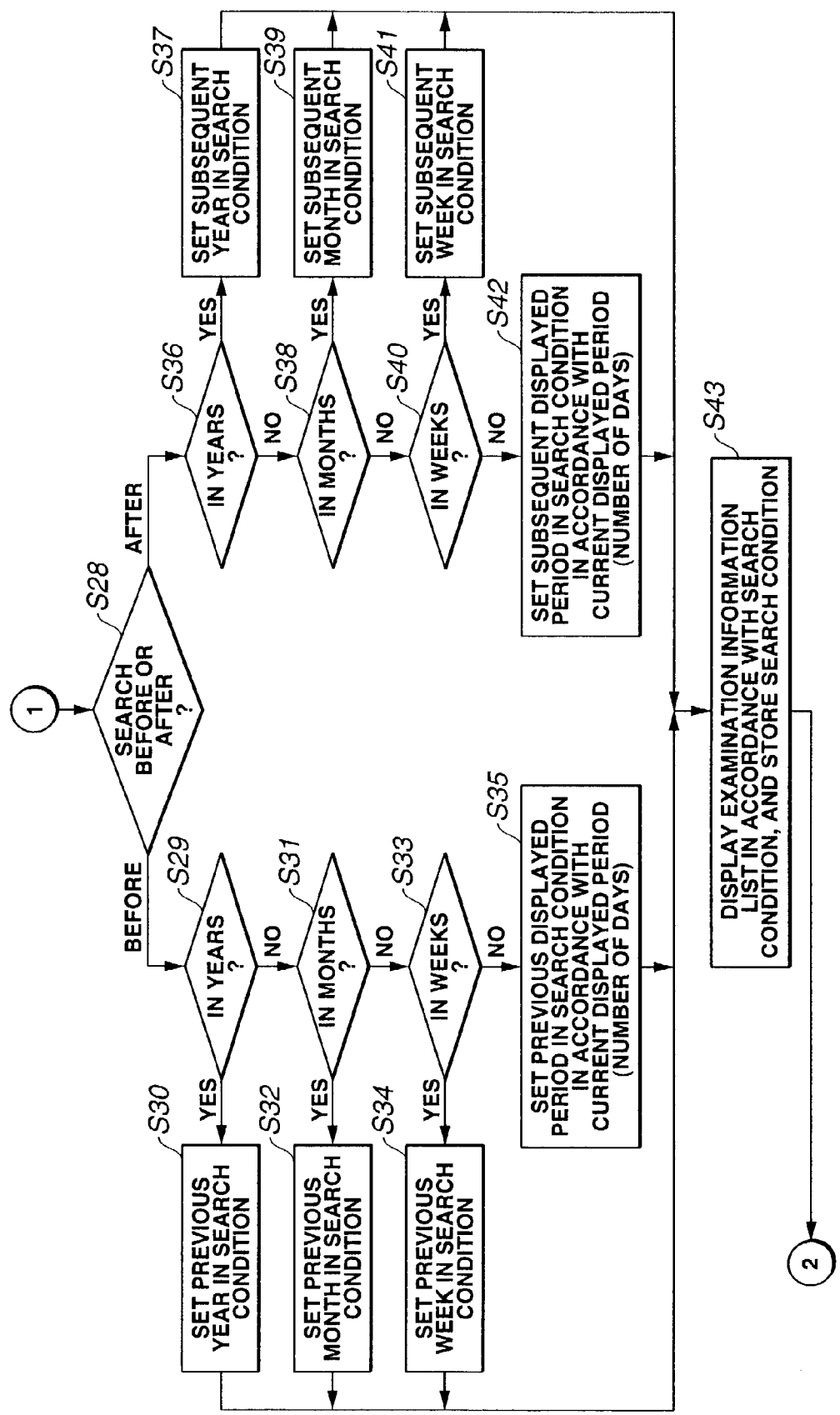

ENDOSCOPE IMAGE FILING SYSTEM AND ENDOSCOPE IMAGE FILING METHOD

This application claims benefit of Japanese Application No. 2001-258469 filed in Japan on Aug. 28, 2001, the contents of which are incorporated by this reference.

BACKGROUND OF THE INVENTION

1. Field of the Invention

The present invention relates to an endoscope image filing system and an endoscope image filing method, in which image signals from an endoscope device are recorded by associating the image signals with examination information relating to an endoscope examination.

2. Description of the Related Art

Endoscope devices have been more widely used than before. An endoscope device has a long and narrow inserting portion, which is inserted to a subject part within a body cavity, for example. An imaging unit is provided in the inserting portion. Then, the endoscope device is arranged to display an image of the subject part imaged by the imaging unit, that is, an endoscope image on a monitor.

Recently, an endoscope device to which an image filing device is connected has been widely used as an endoscope image filing system. The image filing device is used for recording endoscope images.

In the endoscope image filing system, when an endoscope switch, such as a release switch, provided in the endoscope device is pressed, an endoscope image displayed on the monitor is recorded in the image filing device.

In addition, the endoscope image filing system can not only record endoscope images but also record various information relating to endoscope examinations such as patient information including patients' names, ages and sexes, endoscope examination reservation information including the reservation date, reservation times and the examination types for endoscope examinations, and examination information including comments by doctors regarding recorded endoscope images, examination date and time when the endoscope examinations are performed.

Furthermore, the endoscope image filing system can retrieve the recorded information by using various searching measures.

However, in the endoscope filing system as described for the related art, when examination information regarding the endoscope examination, which is recorded in the system, is searched repeatedly by using similar search conditions, a screen on which the search condition is input must be opened every time, which takes time.

SUMMARY OF THE INVENTION

Accordingly, it is an object of the present invention to provide an endoscope image filing system and an endoscope image filing method, which can improve operability when examination information regarding an endoscope examination recorded in the system, is searched.

According to one aspect of the present invention, there is provided an endoscope image filing system having an image filing device recording image signals output from an endoscope device by associating with examination information relating to an endoscope examination, including: an endoscope examination information recording unit for recording the examination information; a search condition input unit for inputting a search condition for searching the examination information; an endoscope examination information search unit for searching the examination information recorded by the endoscope examination information recording unit in accordance with the input search condition; a before/after search setting unit for setting a before/after search condition in order to change a search range under a condition predetermined for the search condition; a before/after search executing unit for searching the examination information recorded by the endoscope examination information recording unit in accordance with the before/after search condition set by the before/after search setting unit; and an examination information display unit for displaying at least one of search results by the endoscope examination information search unit and the before/after search executing unit.

According to another aspect of the present invention, there is provided an endoscope image filing method having an image filing device recording image signals output from an endoscope device by associating with examination information relating to an endoscope examination, including: an endoscope examination information recording step for recording the examination information; a search condition input step for inputting a search condition for searching the examination information; an endoscope examination information search step for searching the examination information recorded by the endoscope examination information recording step in accordance with the input search condition; a before/after search setting step for setting a before/after search condition in order to change a search range under a condition predetermined for the search condition; a before/after search executing step for searching the examination information recorded by the endoscope examination information recording step in accordance with the before/after search condition set by the before/after search setting step; and an examination information display step for displaying at least one of search results by the endoscope examination information search step and the before/after search executing step.

These and the other features and advantages of the present invention will be fully apparent from the description below.

BRIEF DESCRIPTION OF THE DRAWINGS

Figure 5:
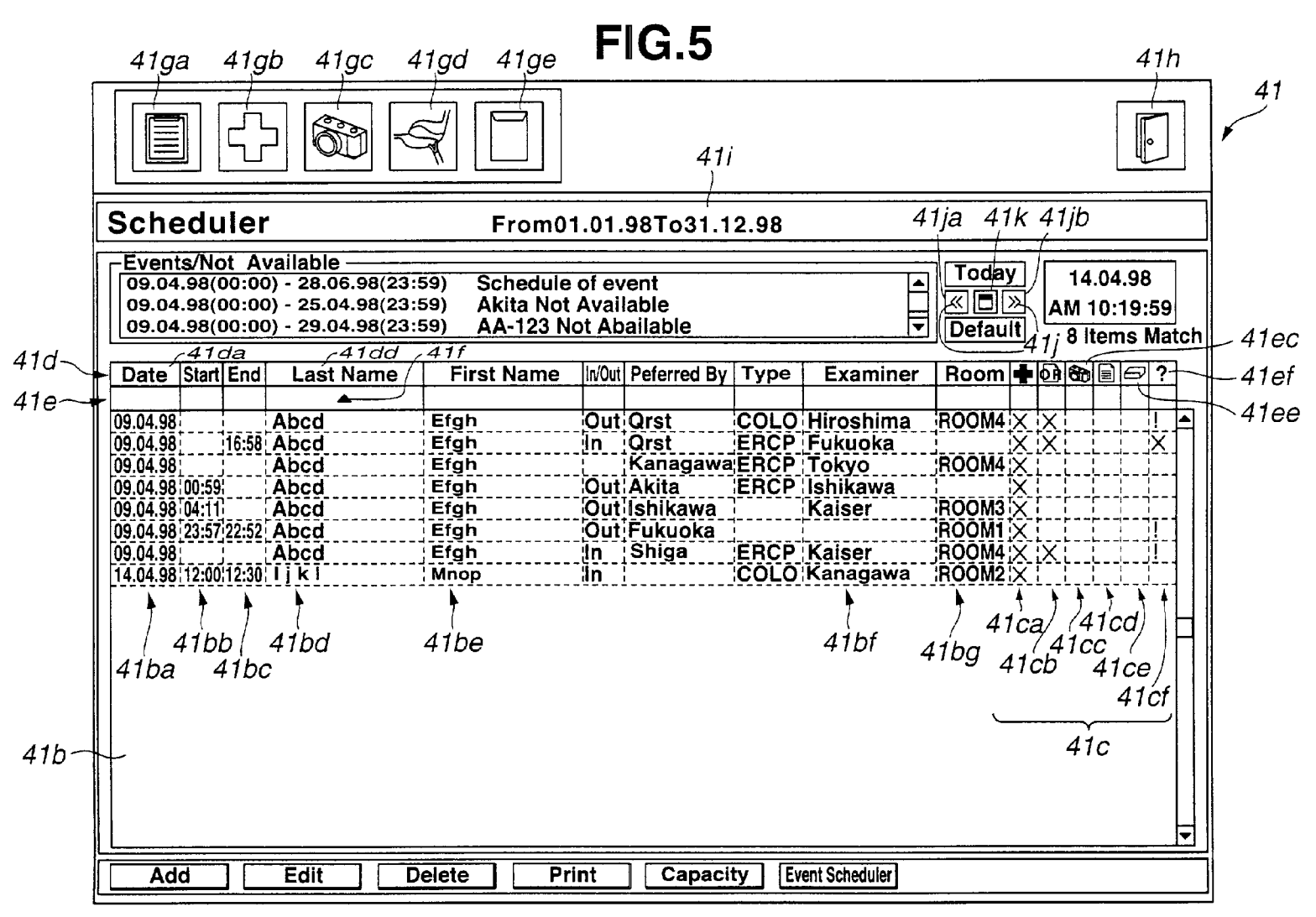

FIG. 5 is a diagram showing a screen display example of a scheduler screen;

Figure 7:
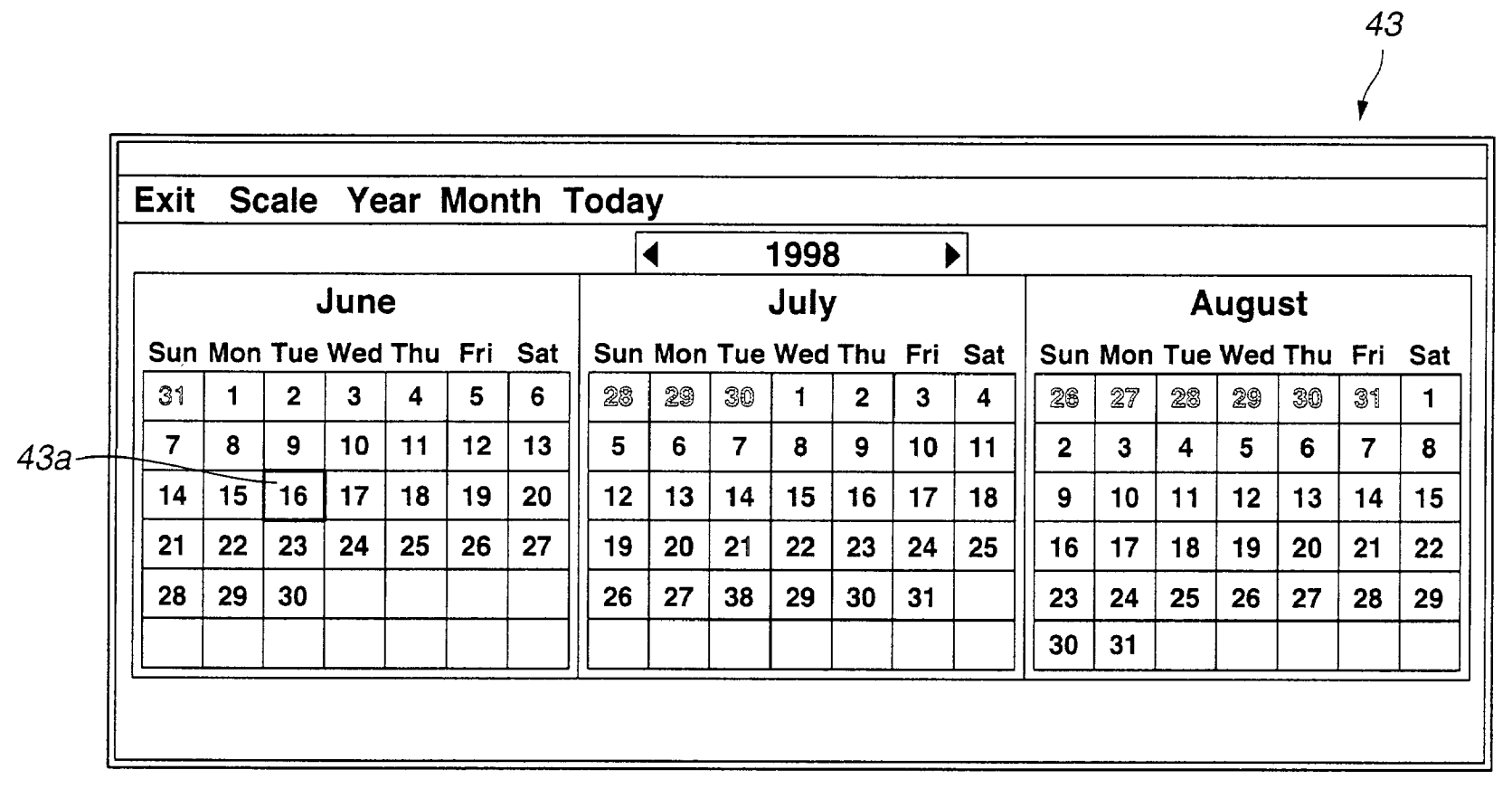

FIG. 7 is a diagram showing a screen display example of a calendar screen;

FIG. 8 is a diagram showing a first display example of a screen for setting a narrowing-down search condition;

FIG. 9 is a diagram showing a display example of the screen for setting a narrowing-down search condition;

FIG. 10 is a diagram showing a second display example of a screen for setting a narrowing-down search condition;

FIG. 12 is a flowchart for explaining a flow returning from a step S27 to a step S23 of FIG. 11.

DETAILED DESCRIPTION OF THE PREFERRED EMBODIMENTS

An embodiment of the present invention will be described below with reference to drawings.

Figure 1:
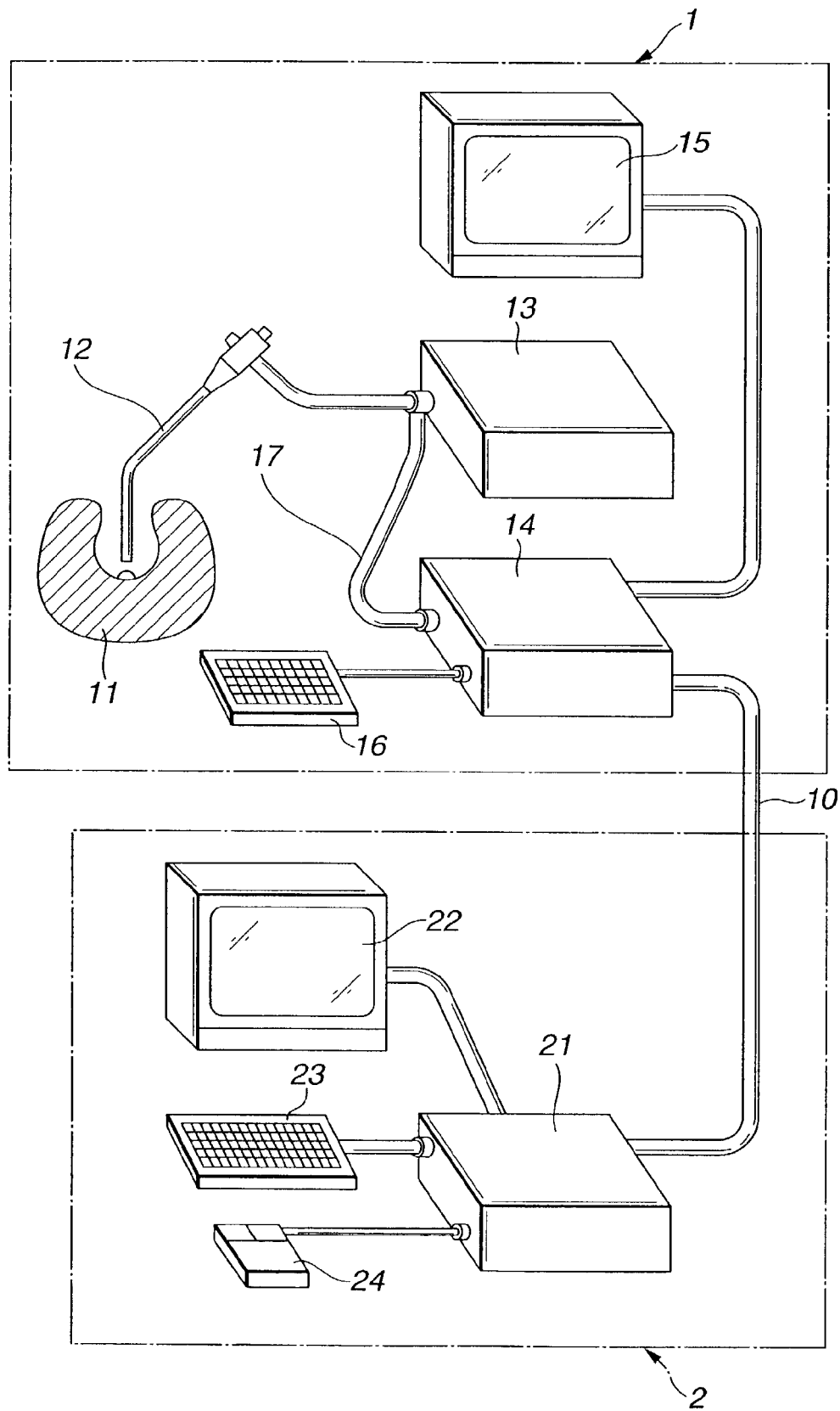
FIG. 1 is an explanatory diagram for explaining the entire construction of an endoscope image filing system.
Figure 2:
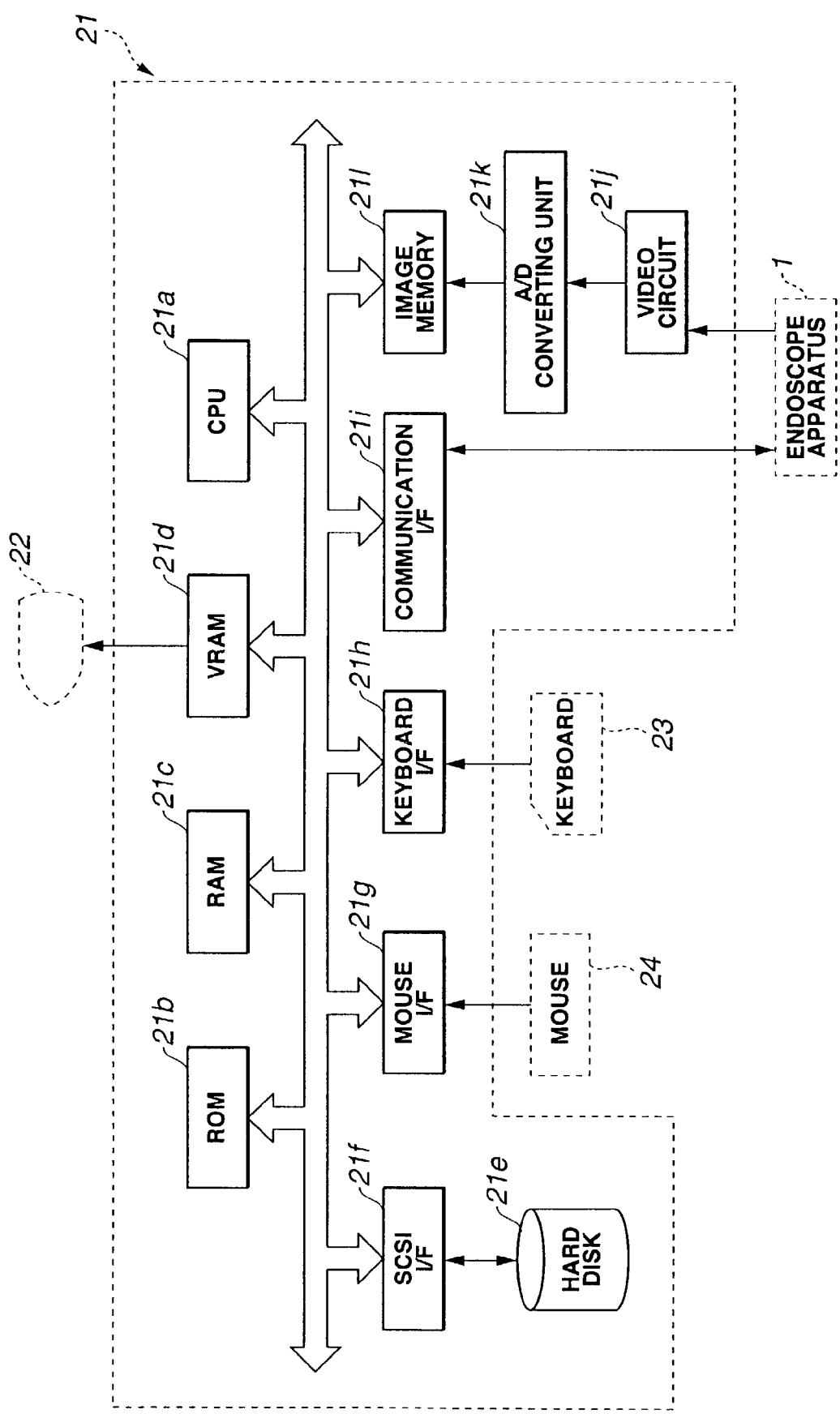
FIG. 2 is a block diagram for explaining the hardware construction of an image filing device.
Figure 3:
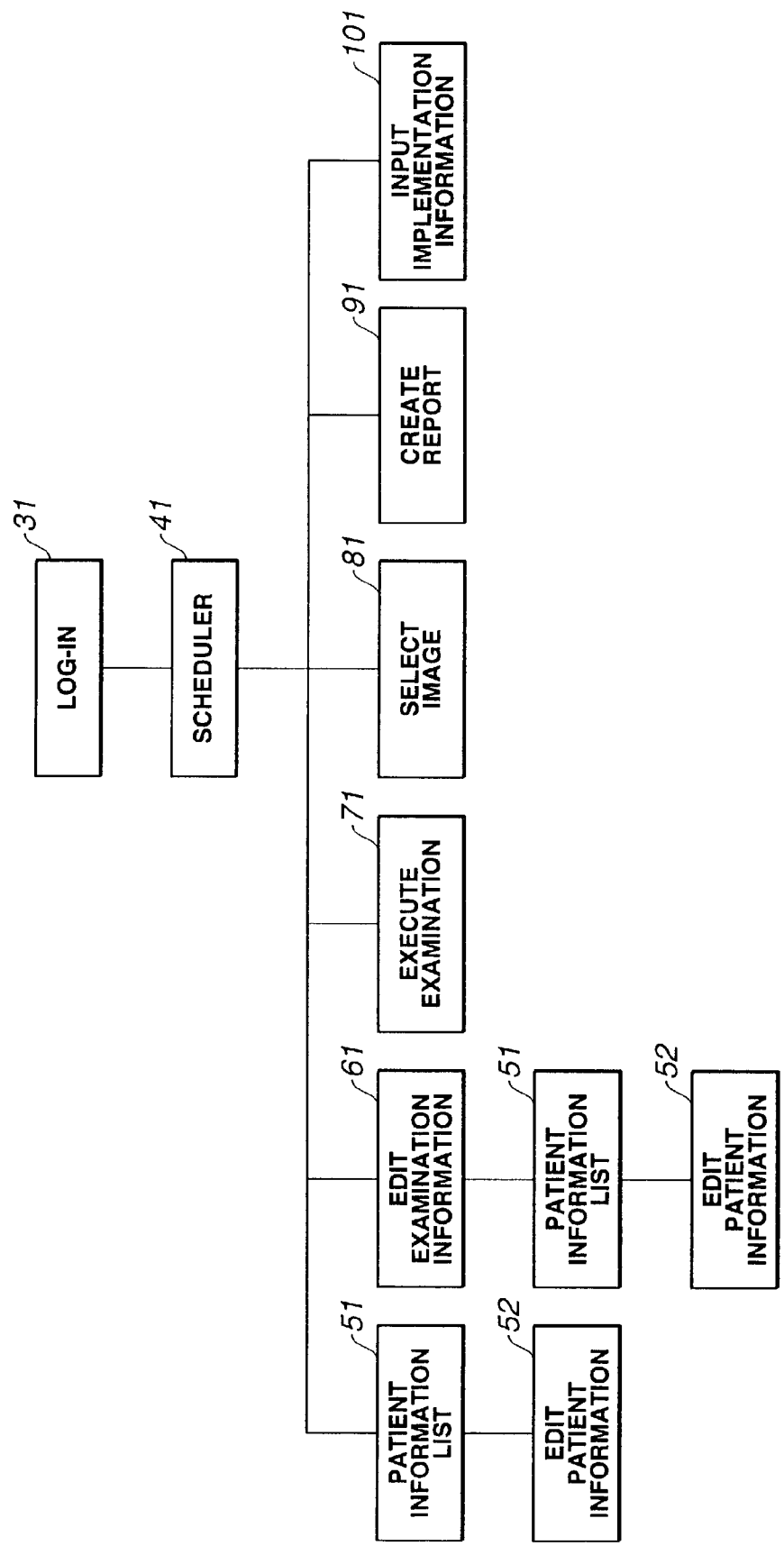
FIG. 3 is an explanatory diagram for explaining an outline of an image construction of the image filing device.
Figure 4:
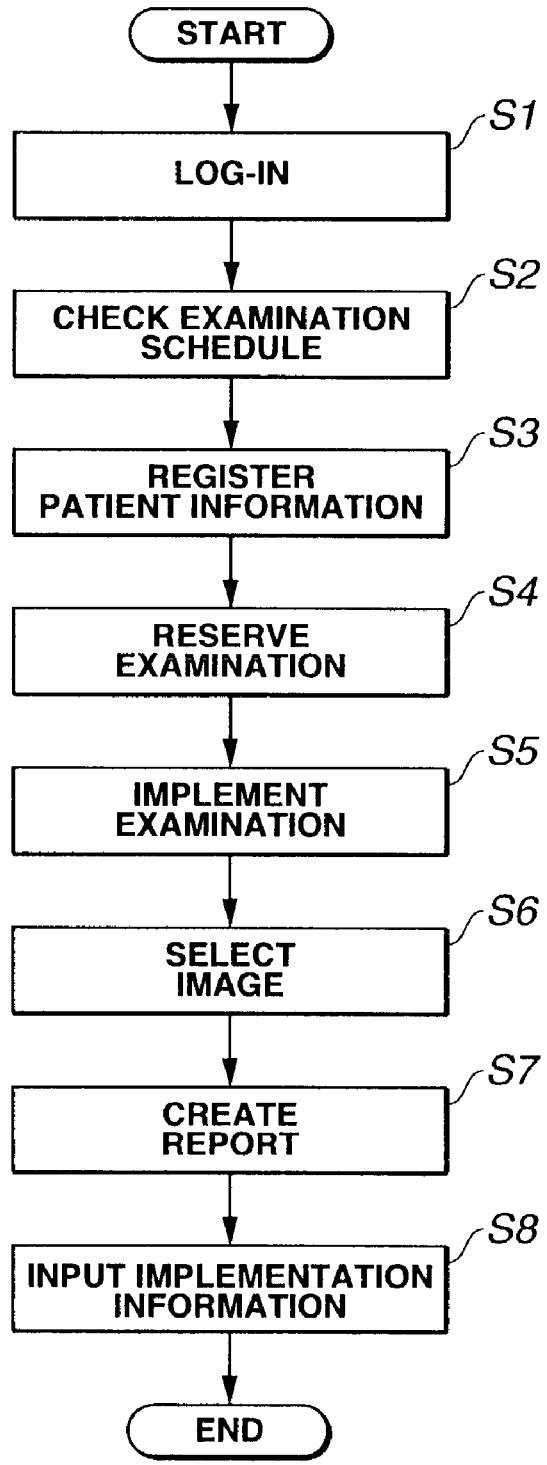
FIG. 4 is a flowchart for explaining an overview of an operational flow of the image filing device.
Figure 6:
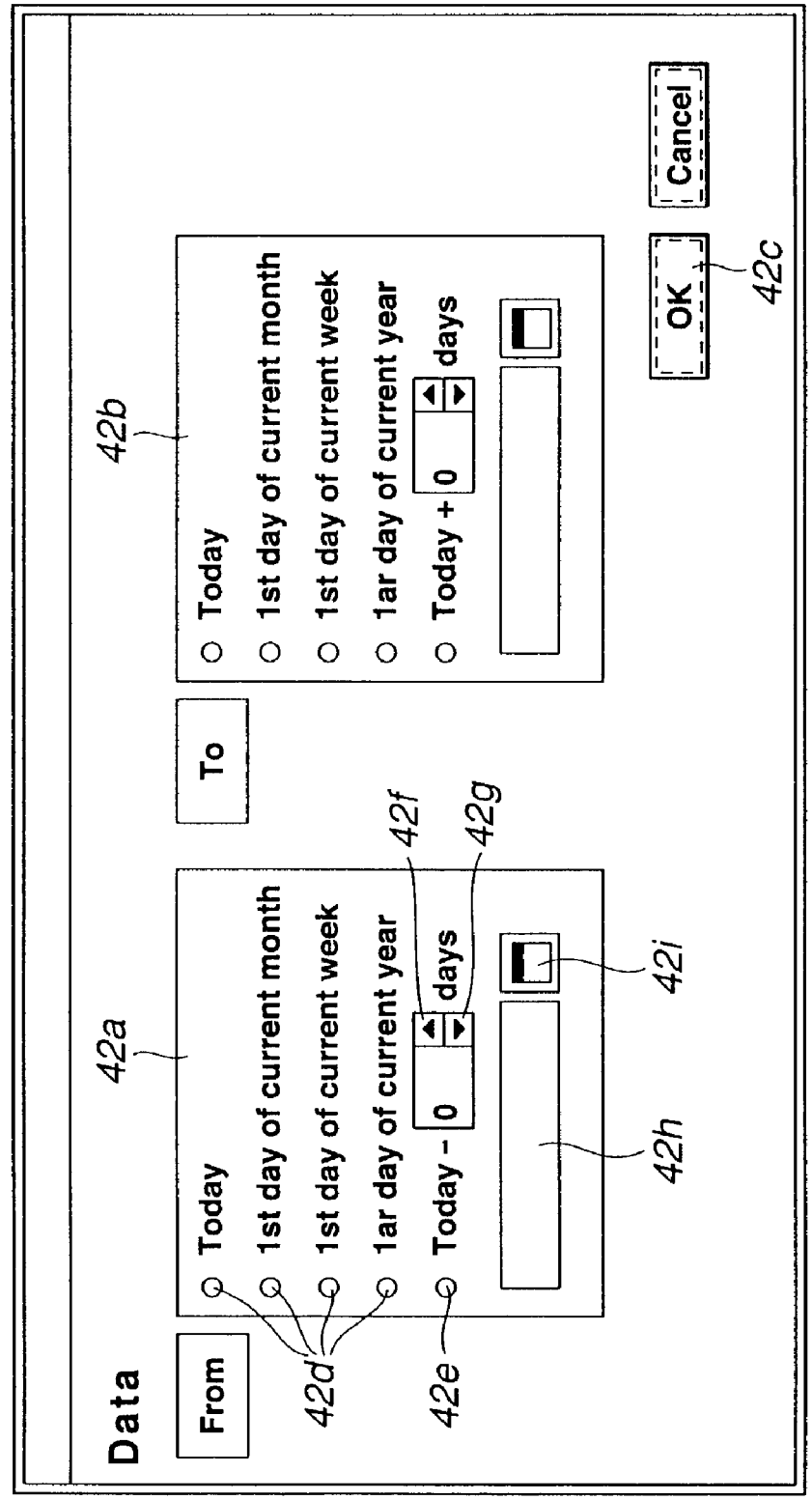
FIG. 6 is a diagram showing a screen display example of a screen for setting a narrowing-down search condition.
Figure 11:
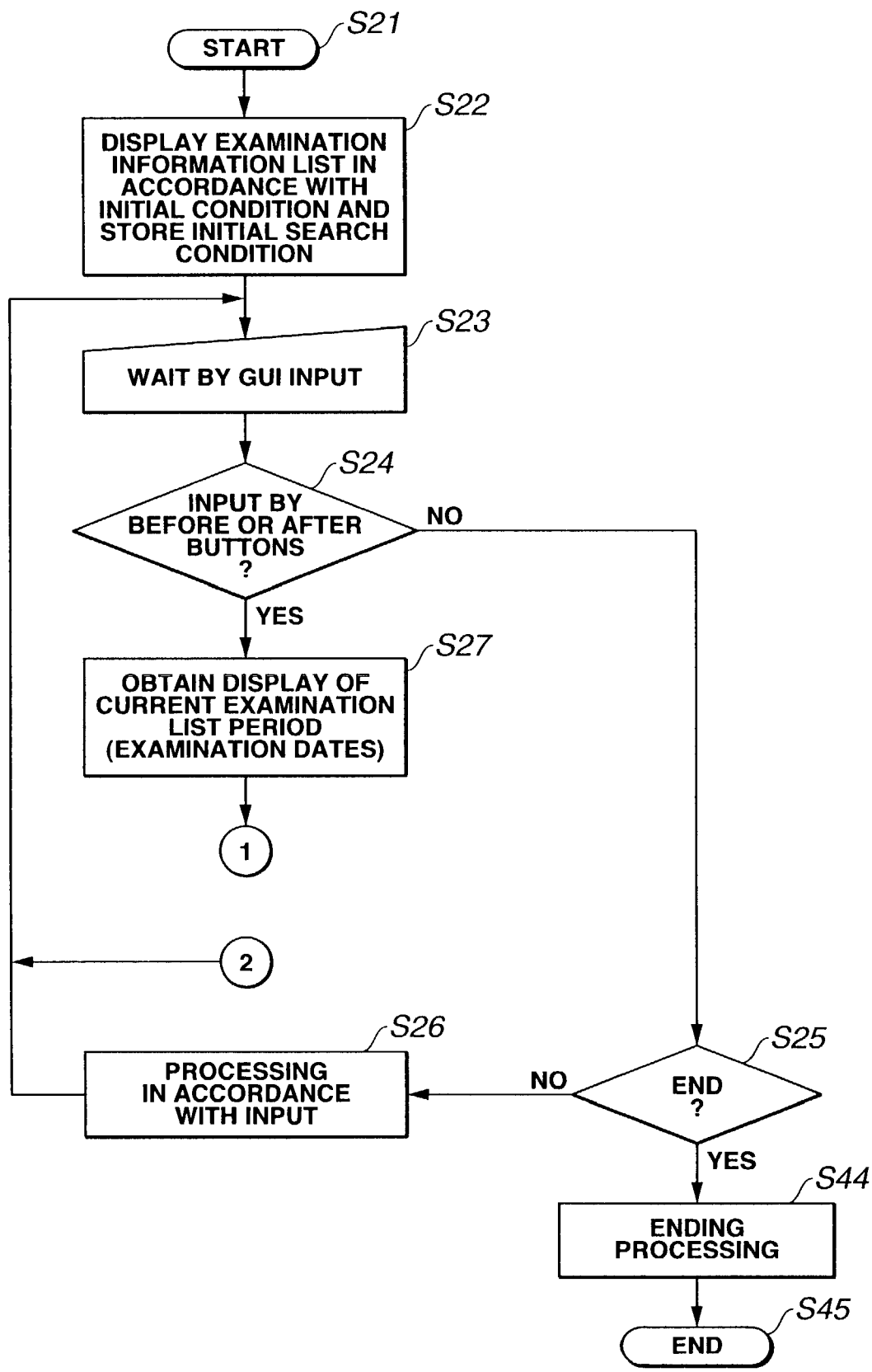
FIG. 11 is a flowchart for explaining a flow of the execution of a before/after search.

FIGS. 1 to 12 relate to an embodiment of the present invention. FIG. 1 is an explanatory diagram for explaining the entire construction of an endoscope image filing system; FIG. 2 is a block diagram for explaining the hardware construction of an image filing device; FIG. 3 is an explanatory diagram for explaining an outline of an image construction of the image filing device; FIG. 4 is a flowchart for explaining an overview of an operational flow of the image filing device; FIG. 5 is a diagram showing a screen display example of a scheduler screen; FIG. 6 is a diagram showing a screen display example of a screen for setting a detail search condition; FIG. 7 is a diagram showing a screen display example of a calendar screen; FIG. 8 is a diagram showing a first display example of a screen for setting a narrowing-down search condition; FIG. 9 is a diagram showing a display example of the screen for setting a narrowing-down search condition; FIG. 10 is a diagram showing a second display example of a screen for setting a narrowing-down search condition; FIG. 11 is a flowchart for explaining a flow of the execution of a before/after search; and FIG. 12 is a flowchart for explaining a flow returning from a step S27 to a step S23 of FIG. 11.

As shown in FIG. 1, an endoscope image filing system according to this embodiment mainly includes an endoscope device 1 and an image filing device 2, which is connected to the endoscope device 1 through a signal transmission cable 10.

The endoscope device 1 mainly includes an electronic endoscope 12, a light source device 13, a video processor (or a video signal processing device) 14, a monitor 15, a keyboard 16 and a signal transmission cable 17.

The electronic endoscope 12 includes an imaging unit. The light source device 13 supplies illuminating light to the electronic endoscope 12. The video processor 14 performs signal processing for the imaging unit of the electronic endoscope 12 to create video signals. The monitor 15 is connected to the video processor 14 and displays images. The keyboard 16 is connected to the video processor 14 and performs manipulation inputs on the video processor 14. The signal transmission cable 17 is used for transmitting image signals and different kinds of data between the electronic endoscope 12 and the light source device 13 and the video processor 14.

The electronic endoscope 12 includes an endoscope imaging unit, whose long and narrow inserting portion is inserted to a subject part of a body cavity, for example, of a patient 11 for the observation. The electronic endoscope 12 supplies to the video processor 14 the image, that is, endoscope image signals of the subject part imaged by the endoscope imaging unit. The video processor 14 creates video signals by performing video signal processing on the endoscope image signals from the endoscope 12 and displays the image on the monitor 15. The endoscope image signals from the electronic endoscope 12 are output to the image filing device 2 through the signal transmission cable 10. In addition, the video processor 14 sends/receives different kinds of data to/from the image filing device 2 through the signal transmission cable 10.

The image filing device 2 includes a personal computer 21, a monitor 22, a keyboard 23 and a mouse 24.

The personal computer 21 receives manipulation inputs from the keyboard 23 and the mouse 24 and video signals are supplied from the endoscope device 1 through the signal transmission cable 10. The personal computer 21 sends/receives different kinds of data to/from the endoscope device 1 through the signal transmission cable 10.

The personal computer 21 records image signals output from the endoscope device 1 associated with examination information regarding an endoscope examination input by using the keyboard 23 and/or the mouse 24 in accordance with a release trigger generated by pressing an endoscope switch, such as a release switch, provided in the electronic endoscope 12. In addition, the personal computer 21 displays image signals and/or information output from the endoscope device on the monitor 22.

Thus, the image filing device 2 records image signals output from the endoscope device 1 and associated with examination information regarding the input endoscope examination in accordance with the release trigger.

The internal construction of the personal computer 21, which is a main part of the image filing device 2, will be described with reference to FIG. 2.

The personal computer 21 includes a CPU 21a, a ROM 21b, a RAM 21c, a VRAM 21d, a hard disk 21e, a hard disk 21e, an SCSI interface portion 21f, a mouse interface portion 21g, a keyboard interface portion 21h, a communication interface portion 21i in the RS232C format, a video circuit 21j, an A/D converting portion 21k, and an image memory 211.

The CPU 21a is a main control unit, which controls different parts of the personal computer 21. The ROM 21b stores programs operating the CPU 21a, messages displayed on the monitor 22 and so on. The RAM 21c is used as a work area for the CPU 21a and a temporally memory area for different kinds of data. The VRAM 21d temporarily stores image data to be output to the monitor 22.

The hard disk 21e stores image data and different kinds of data. The SCSI interface portion 21f sends/receives data in the publicly known SCSI format to/from hard disk 21e.

The mouse interface 21g detects an input from the mouse 24. The keyboard interface portion 21h detects an input from the keyboard 23. The communication interface portion 21i is an interface in the publicly known RS232C format and sends/receives different kinds of data to/from the endoscope device 1.

The video circuit 21j is an interface circuit, which inputs image signals output from the endoscope device 1. The A/D converting portion 21k A/D converts image signals input by the video circuit 21j. The image memory 211 temporarily stores image data output from the A/D converting portion 21k.

In this case, the hard disk 21e is used as an endoscope examination information recording unit, which records examination information regarding an endoscope examination.

The keyboard 23 and the mouse 24 are search condition input units, which are used for inputting a search condition to search the examination information.

The CPU21a, the ROM 21b and the RAM 21c function as endoscope examination information searching units, which are used for searching the examination information recorded by the endoscope examination information recording unit in accordance with the input search condition.

In addition, the CPU 21a, the ROM 21b, and the RAM 21c function as a before/after search setting unit, which are used for setting the before/after search condition in order to change a search range in accordance with a predetermined condition with respect to the search condition.

Furthermore, the CPU 21*a*, ROM 21*b* and the RAM 21*c* function as a before/after executing unit, which are used for searching the examination information recorded by the endoscope examination information recording unit in accordance with the before/after search condition set by the before/after search setting unit.

The monitor 22 and the VRAM 21*d* function as examination information display unit, which is used for displaying at least one of the search results by the endoscope examination information searching unit and the before/after search executing unit.

Additionally, the keyboard 23 and the mouse 24 function as a before/after search selecting unit, which is used for selecting a search by the before/after search executing unit. The before/after search executing unit searches the examination information in accordance with the selection by the before/after search selecting unit.

In this way, the image filing device 2 having the personal computer 21 as the main part can display image data obtained by the endoscope device 1 on the monitor 22 and can store them in the hard disk 21*e*.

In order to perform processing in the image filing device 2, an operator inputs data and/or an instruction by using the keyboard 23 and/or the mouse 24 in accordance with different kinds of screens displayed on the monitor 22. Then, the CPU 21*a* controls parts corresponding to the input data and/or instruction. In other words, the image filing device 2 performs different kinds of processing in accordance with the flow in the screen displayed on the monitor 22.

An outline of the screen construction of the image filing device 2 will be described with reference to FIG. 3.

First of all, when the image filing device 2 is started, a log-in screen 31 is displayed in which an operator is authenticated.

The image filing device 2 displays a scheduler screen 41 in which a list of examination schedules are displayed when the operator is authenticated in the log-in screen 31.

The scheduler screen 41 can call up an examination information editing screen 61 where patient information can be edited.

The scheduler screen 41 can call up an examination executing screen 71 where an examination is executed by connecting to the endoscope device 1 and images can be captured from the endoscope device 1.

The scheduler screen 41 can call up an image selecting screen 81 where an image among captured images is selected for the examination report to be created.

In addition, the scheduler screen 41 can call up a report creating screen 91, which is a screen where the examination report can be created.

Furthermore, the scheduler screen 41 can call up a implementation information input screen 101 where a diagnosis code, an accounting code and so on relating to the examination can be input and be checked.

An example of an entire flow of an operation on the image filing device 2 will be described with reference to FIG. 4. Notably, reference numerals S1 to S8 in FIG. 4 are given to processing steps.

First of all, an operator starts the endoscope image filing device 2. Then, the endoscope image filing device 2 displays a log-in screen 31 on the monitor 22. Under this condition, the operator performs manipulations such as a password input by using the keyboard 23 and/or mouse 24. Here, the personal computer 21 authenticates the operator, and, at a step S1, the operator logs in. Thus, the endoscope image filing device 2 displays the scheduler screen 41 on the monitor 22. Here, at a step S2, the operator checks the examination schedule.

Next, at a step S3, when the examined patient is a new patient, the operator calls up the patient list screen 51 and the patient information editing screen 52 and registers the patient information by using the keyboard 23 and/or the mouse 24.

Next, at a step S4, the operator calls up the examination information editing screen 61 and inputs a new examination reservation.

Next, at a step S5, the operator calls up the examination executing screen 71 and executes an examination by using the endoscope device 1 connected to the image filing device 2. The images obtained by the endoscope device 1 are stored in the image filing device 2.

Next, at a step S6, the operator calls up the image selecting screen 81 and selects an image, among the images in the examination execution, referred in the examination report to be created.

Next, at a step S7, the operator calls up the report creating screen 91 and creates the examination report.

Next, at a step S8, the operator calls up the implementation information input screen 101 and inputs the diagnosis code, the accounting code and so on relating to the examination.

The above-described flow is the example of the entire flow of the operation.

The more detail construction and operations for respective screens will be described below.

FIG. 5 is a screen display example of the scheduler screen 41.

In the scheduler screen 41, an examination information list display area 41*b* is located for displaying a list of examination information.

One piece of examination information is called "examination information record" herein.

The first line of the examination information display area 41*b* displays headings corresponding to data items included in an examination information record.

The examination information record is displayed from the third row of the examination information list display area 41*b*. One examination information record is displayed in one row of the examination information list display area 41*b*.

The data items included in the examination information record include an examination date 41*ba*, a starting time 41*bb*, an ending time 41*bc*, the last name of the patient 41*bd* and the first name of the patient 41*be* for the examination, an examiner name 41*bf*, a name 41*bg* of a used examination room and so on.

An examination status display field group 41*c* for displaying a status, such as a progress, of works relating to the examination is located in the examination information display area 41*b*.

An examination status display field 41*ca* included in the examination status display field 41*c* displays a distinction indicating whether or not the input required items of examination information and the input required items of the information regarding the patient to be examined have been input. For example, when the input required items of the examination information and the input required items of the information regarding the patient to be examined have been all input, "x" is displayed in the examination status display field 41*ca*. Otherwise, the examination status display field 41*ca* is left empty.

The examination status display field 41*bc* displays a distinction indicating whether or not the data when a written agreement for the examination is received from the patient is input. For example, when the date when the written agreement of the examination is received from the patient has been already input, "x" is displayed in the examination status display field 41cb. Otherwise, the examination status display field 41cb is left empty. The examination status display field 41cc displays a distinction indicating whether or not images of the examination have been recorded. For example, when the examination has been already executed, the number of images recorded in the examination is displayed in the examination status display field 41cc. When the examination has not been executed, the examination status display field 41cc is left empty. In other words, a number displayed in the examination status display field 41cc means that images of the subject part of the patient have been obtained by the examination.

The display status display field 41cd displays a distinction indicating whether or not an examination report has been created. For example, when the examination report has been created, the "x" is displayed in the examination status display field 41cd. When the examination report has not been created yet, the examination status display field 41cd is left empty.

The examination status display field 41ce displays a distinction indicating whether or not an accounting code has been input. When the accounting code has been input already, "x" is displayed in the examination status display field 41ce. When the accounting code has been input but some change occurs therein, "!" is displayed in the examination status display field 41ce. When the accounting code has been input but the applicable data is not present, "o" is displayed in the examination status display field 41ce. When the accounting code has not been input yet, the examination status display field 41ce is left empty.

The examination status display field 41cf displays a distinction indicating a result status of a living body examination, for which a living body organization is taken in the endoscope examination. For example, when the living body examination has been implemented and the examination result has been already obtained, "x" is displayed in the examination status display field 41cf. When living body examination has been performed but the examination result has not been obtained yet, "!" is displayed in the examination status display field 41cf. When the endoscope examination has been implemented but the living body examination has not been implemented, "o" is displayed in the examination status display field 41cf. When the endoscope examination has not been implemented yet, the examination status display field 41cf is left empty.

The examination information list display area 41b can not only display all of the examination information records but also display interested examination information records specifically.

Positions of data items in the first row, that is, in a row where item names of data items are displayed are provided with a filter button group 41d to be used for calling up a screen on which a narrowing-down condition can be set in each of the data items.

Each in the filter button group 41d is at the convex state when no narrowing-down condition is specified in the corresponding data item.

The button at the convex state is a button under a condition where a shade is displayed so that the button can appear isolated on the screen. On the other hand, a button at the concave state is a button under a condition where a shade is displayed so that the button can appear concave on the screen.

Here, the operator clicks a convex button in the filter button group 41d by using the mouse 24. Then, the image filing device 2 opens a narrowing-down condition setting screen, which will be described later, for setting a narrowing-down condition in the corresponding data item. Here, the operator inputs a narrowing-down condition so that only the examination information record, which can satisfy the narrowing-down condition, can be displayed in the examination information list display area 41b.

Each in the filter button group 41d becomes concave when the button corresponds to the data item for which the narrowing-down condition is set.

When there are multiple concave buttons in the filter button group 41d, examination information records are narrowed down by applying AND to the narrowing-down conditions specified in each of the filter button group 41d. Then, the specific examination information records are displayed in one row of the examination information list display area 41b.

Here, the operator clicks a concave button of the filter button group 41d. Then, the narrowing-down condition, which is specified for the corresponding data item, is released. Then, the button of the filter button group 41d becomes convex.

Here, a flow of operations performed when a narrowing-down condition is specified for the examination date 41ba, for example, will be described.

An operator clicks a filter button 41da at a position corresponding to the examination date 41ba by using the mouse 24. Then, the image filing device 2 calls up a narrowing-down condition setting screen 42 shown in FIG. 6, which is used for setting a narrowing-down condition in the examination date 41ba.

On the narrowing-down condition setting screen 42, the operator specifies dates in a setting field 42a for a narrowing-down start date and a setting filed 42b for a narrowing-down end date, respectively.

Then, the narrowing-down condition setting screen 42 is closed and the filter button 41da becomes concave. Then, only the examination information records between the dates specified in the setting fields 42a and 42b are displayed in the examination dates 41ba in the examination information list display area 41b.

When the operator inputs either one of the current date, the first date of the current month, the first date of the current week and the first date of the current year is input in each of the setting fields 42a and 42b, one of a button group 42d corresponding to the items can be clicked and selected by using the mouse 24. In addition, the number of dates with respect to the current date can be set in each of the setting fields 42a and 42b. In this case, the operator can click a button 42e corresponding to the item by using the mouse 24. Then, the number of relative dates can be set by clicking a button 42f and a button 42g, which increases and decreases one day each, respectively, by using the mouse 24. Furthermore, the operator can input the year, the month and/or the day in an input field 42h by using the keyboard 23.

The operator can click a calendar-calling button 42i by using the mouse 24 so that a calendar screen 43 shown in FIG. 7 can be called up. In this case, when a date button 43a displayed on the calendar screen 43 is clicked so that a date corresponding to the date button 43a can be input in the input field 42h so as to set the date.

The year and the month to be displayed on the calendar screen 43 can be changed by using the mouse 24. Thus, any desired year, month and/or day can be selected.

When the operator clicks a filter button 41dd corresponding to the last-name position 41bd, for example in the examination information list display area 41b shown in FIG. 5, a narrowing-down condition setting screen 44 shown in FIG. 8 is called up for setting a condition of patient's last name to be narrowed down.

The operator can input patient's last name in an input field 44a on the narrowing-down condition setting screen 44b by using the keyboard 23 and click an OK button 44b. Then, the image filing device 2 displays only the examination information record corresponding to the patient having the input last name in the examination information list display area 41b. Notably, in order to narrow down the condition for patient's last name, last names completely matching with the input string may be searched in the input field 44a. Alternatively, last names including the string can be searched.

Furthermore, the operator can click, for example, filter button 41ec corresponding to the examination status display field 41cc indicating whether or not the examination has been finished in the examination information list display area 41b shown in FIG. 5 by using the mouse 24. Then, the image filing device 2 calls up a narrowing-down condition setting screen 45, as shown in FIG. 9, which is used for setting to use the distinction indicating whether or not the examination has been done or not as a narrowing-down condition.

The operator clicks and selects either one of distinctions indicating the examination has been done and has not been done, respectively, in the setting field 45a of the narrowing-down condition setting screen 45 and clicks an OK button 45b. Then, the image filing device 2 displays, in the examination information list display area 41b, only the examination information records each having the status in the examination status display field 41 cc matching with the setting in the setting field 45a.

In the examination information list display area 41b shown in FIG. 5, the operator may click, for example, a filter button 41ee corresponding to the examination status display field 41ce indicating a distinction regarding the accounting code. Then, the image filing device 2 calls up a narrowing-down condition setting screen 46, as shown in FIG. 10, for setting to use, as a narrowing-down condition, the distinction indicating whether or not the accounting code has been input. The operator clicks and selects a distinction indicating the status of the accounting code input in the setting field 46a on the narrowing-down condition setting screen 46 and clicks an OK button 46b by using the mouse 24. Then, the image filing device 2 displays, in the examination information list display area 41b, only the examination information record having the examination status display field 41ce matching with the setting field 46a.

Next, a flow of the execution of before/after searches for the examination information list display will be described with reference to a flowchart shown in FIG. 11. Reference numerals S21 to S45 in FIG. 11 are given to processing steps.

The personal computer 21 authenticates an operator. Then, at the step S1 in FIG. 4, the operator logs in, and the scheduler screen 41 is called up in the monitor 22. Then, the personal computer 21 starts to display the examination information list at a step S21 in FIG. 11.

Once the personal computer 21 starts to display the examination information list, examination information is searched in accordance with an initial narrowing-down condition and displays a corresponding examination record in the examination information list display area 41b at a step S22.

Next, the personal computer 21 waits for a button input on the scheduler screen at a step S23.

When a button input is performed by manipulating, for example, the mouse 24 at a step S23, the personal computer 21 checks whether or not the input button is a date before/after button 41j at a step S24.

When the input is not through the date before/after button 41j at the step S24, the personal computer 21 checks whether or not the input button is an end button or not at a step S25. If the input button is the end button, the personal computer 21 performs end processing at a step S44. Then, the execution of the before/after search ends at a step S45. In other words, the schedule display screen is closed.

If the input button is not the end button at the step S25, the personal computer 21 performs processing in accordance with the input button at a step S26. Then, the processing returns to the step S23. At the step S26, the personal computer 21 searches examination information in accordance with the search condition input by using the input button. Then, the personal computer 21 performs processing such as displaying the corresponding examination record in the examination information list display area 41b.

If the input is through the date before/after button 41j at the step S24, the personal computer 21 obtains, at a step S27, information specified by the filter button 41da used for the search through the examination list displayed in the examination list display area 41b currently, that is, information regarding the start date and the end date for the narrowing-down.

Next, the personal computer 21 checks whether the input button is the before search button 41ja or the after search button 41jb.

If the input button is the before search button 41ja at a step S28, the personal computer 21 checks whether or not the information regarding the narrowing-down start date and the narrowing-down end date obtained at the step S27 is set in years at a step S29.

If the information regarding the narrowing-down start date and the narrowing-down end date obtained at the step S27 is set in years at the step S29, the personal computer 21 sets the narrowing-down start date and the narrowing-down end date so as to obtain information one year ago set by the filter button 41da at a step S30.

If the information regarding the narrowing-down start date and the narrowing-down end date obtained at the step S27 is not set in years at the step S29, the personal computer 21 checks whether or not the information regarding the narrowing-down start date and the narrowing-down end date obtained at the step S27 is set in months at a step S31.

If the information regarding the narrowing-down start date and the narrowing-down end date obtained at the step S27 is set in months at the step S31, the personal computer 21 sets the narrowing-down start date and the narrowing-down end date so as to obtain information one month ago set by the filter button 41da at a step S32.

If the information regarding the narrowing-down start date and the narrowing-down end date obtained at the step S27 is not set in months at the step S31, the personal computer 21 checks whether or not the information regarding the narrowing-down start date and the narrowing-down end date obtained at the step S27 is set in weeks at a step S33.

If the information regarding the narrowing-down start date and the narrowing-down end date obtained at the step S27 is set in weeks at the step S33, the personal computer 21 sets the narrowing-down start date and the narrowing-down end date so as to obtain information one week ago set by the filter button 41*da* at a step S34.

If the information regarding the narrowing-down start date and the narrowing-down end date obtained at the step S27 is not set in weeks at the step S33, the personal computer 21 sets the information regarding the narrowing-down start date and the narrowing-down end date obtained at the step S27 to the information N day(s) ago, where N is a number of day(s) between the narrowing-down start date and the narrowing-down end date so as to obtain information at a step S35.

If the button input at the step S28 is the after search button 41*jb*, the personal computer 21 checks whether or not the information regarding the narrowing-down start date and the narrowing-down end date obtained at the step S27 is set in years at a step S36.

If the information regarding the narrowing-down start date and the narrowing-down end date obtained at the step S27 is set in years at the step S36, the personal computer 21 sets the narrowing-down start date and the narrowing-down end date so as to obtain information after one year set by the filter button 41*da* at a step S37.

If the information regarding the narrowing-down start date and the narrowing-down end date obtained at the step S27 is not set in years at the step S36, the personal computer 21 checks whether or not the information regarding the narrowing-down start date and the narrowing-down end date obtained at the step S27 is set in months at a step S38.

If the information regarding the narrowing-down start date and the narrowing-down end date obtained at the step S27 is set in months at the step S38, the personal computer 21 sets the narrowing-down start date and the narrowing-down end date so as to obtain information after one month set by the filter button 41*da* at a step S39.

If the information regarding the narrowing-down start date and the narrowing-down end date obtained at the step S27 is not set in months at the step S38, the personal computer 21 checks whether or not the information regarding the narrowing-down start date and the narrowing-down end date obtained at the step S27 is set in weeks at a step S40.

If the information regarding the narrowing-down start date and the narrowing-down end date obtained at the step S27 is set in weeks at the step S40, the personal computer 21 sets the narrowing-down start date and the narrowing-down end date so as to obtain information after one week set by the filter button 41*da* at a step S41.

If the information regarding the narrowing-down start date and the narrowing-down end date obtained at the step S27 is not set in weeks at the step S40, the personal computer 21 sets the information regarding the narrowing-down start date and the narrowing-down end date obtained at the step S27 to the information after N day(s), where N is a number of day(s) between the narrowing-down start date and the narrowing-down end date so as to obtain information at a step S42.

Next, at a step S43, the personal computer 21 searches examination information in accordance with the set narrowing-down condition and displays the examination record(s) corresponding to the examination information list display area 41*b*. Then, the processing is returned to the step S23.

With the construction and processing, the endoscope image filing system includes: an endoscope examination information recording step (steps S1 to S8) for recording the examination information; a search condition input step (steps S22 and S23) for inputting a search condition for searching the examination information; an endoscope examination information search step (step S26) for searching the examination information recorded by the endoscope examination information recording step in accordance with the input search condition; a before/after search setting step (steps S27 to S42) for setting a before/after search condition in order to change a search range under a condition predetermined for the search condition; a before/after search executing step (step S43) for searching the examination information recorded by the endoscope examination information recording step in accordance with the before/after search condition set by the before/after search setting step; and an examination information display step (step S43) for displaying at least one of search results by the endoscope examination information search step and the before/after search executing step.

According to the embodiment of the present invention, examination information relating to endoscope examinations owned by the image filing device 2 are displayed in a list in accordance with a search result under a search condition input by a user. When the search relating to before or after the search condition, the search condition is not input. Instead, the search condition can be specified by using the date before/after button 41*j*. Thus, the operability can be improved when the examination information relating to endoscope examinations stored in the system is searched.

It is obvious that different embodiments in a wider range can be constructed based on the present invention without departing from the spirit and the scope of the present invention. The present invention is not limited by the specific embodiments except for the appended claims.

What is claimed is:

1. An endoscope image filing system having an image filing device recording image signals output from an endoscope device by associating with examination information relating to an endoscope examination, comprising:

endoscope examination information recording means for recording the examination information;

search condition input means for inputting a search condition for searching the examination information;

endoscope examination information search means for searching the examination information recorded by the endoscope examination information recording means in accordance with the input search condition;

before/after search setting means for setting a before/after search condition in order to change a search range under a condition predetermined for the search condition;

before/after search executing means for searching the examination information recorded by the endoscope examination information recording means in accordance with the before/after search condition set by the before/after search setting means, said before/after search executing means having a before portion for decrementing said search range by said before/after search condition and an after portion for incrementing said search range by said before/after search condition; and examination information display means for displaying at least one of search results by the endoscope examination information search means and the before/after search executing means.

2. An endoscope image filing system according to claim 1, further comprising before/after search selecting means for selecting a search by the before/after search executing means, wherein the before/after search executing means searches the examination information in accordance with the selection by the before/after search selecting means.

3. An endoscope image filing method having an image filing device recording image signals output from an endoscope device by associating with examination information relating to an endoscope examination, comprising:
- an endoscope examination information recording step for recording the examination information;
- a search condition input step for inputting a search condition for searching the examination information;
- an endoscope examination information search step for searching the examination information recorded by the endoscope examination information recording step in accordance with the input search condition;
- a before/after search setting step for setting a before/after search condition in order to change a search range under a condition predetermined for the search condition;
- a before/after search executing step for searching the examination information recorded by the endoscope examination information recording step in accordance with the before/after search condition set by the before/after search setting step said before/after search execution step being configured for selectively executing a search before process for decrementing said search range by said before/after search condition or a search after process for incrementing said search range by said before/after search condition; and
- an examination information display step for displaying at least one of search results by the endoscope examination information search step and the before/after search executing step.

4. An endoscope image filing system according to claim 1, the image filing device comprising:
- the endoscope examination information search means for searching the examination information recorded by the endoscope examination information recording means in accordance with the search condition input from the search condition input means;
- the before/after search setting means for changing a search range under a condition predetermined for the search condition input from the search condition input means;
- the before/after search executing means for searching the examination information recorded by the endoscope examination information recording means based on the changed search range; and
- the examination information display means for displaying a search result by the endoscope examination information recording means or the before/after search executing means.

5. An endoscope image filing system according to claim 1, the image filing device comprising a personal computer as a main part, wherein the personal computer includes a CPU, a ROM, a RAM, a VRAM, a hard disk, a keyboard interface portion, a mouse interface portion, a communication interface portion, a video circuit, an A/D converting portion and an image memory.

6. An endoscope image filing system according to claim 2, the image filing device comprising:
- the endoscope examination information search means for searching the examination information recorded by the endoscope examination information recording means in accordance with the search condition input from the search condition input means;
- the examination information display means for displaying the examination information, which is the search result;
- the before/after search selecting means for selecting a search by the before/after search executing means based on the displayed search result;
- the before/after search setting means for changing a search range under the predetermined condition based on the selection by the before/after search selecting means;
- the before/after search executing means for searching the examination information recorded by the endoscope examination information recording means based on the changed search range and in accordance with a selection by the before/after search selecting means; and
- the examination information display means for displaying the examination information, that is the search result.

7. An endoscope image filing system according to claim 2, the image filing device comprising a personal computer as a main part, wherein the personal computer includes a CPU, a ROM, a RAM, a VRAM, a hard disk, a keyboard interface portion, a mouse interface portion, a communication interface portion, a video circuit, an A/D converting portion and an image memory.

8. An endoscope image filing method according to claim 3, causing the image filing device to execute:
- the endoscope examination information search step for searching the examination information recorded by the endoscope examination information recording step in accordance with the search condition input from the search condition input step;
- the before/after search setting step for changing a search range under the condition predetermined for the search condition input by the search condition input step;
- the before/after search executing step for searching the examination information recorded by the endoscope examination information recording step based on the changed search range; and
- the examination information display step for displaying search results by the endoscope examination information recording step or the before/after search executing step.

9. An endoscope image filing method according to claim 3, further comprising a before/after search selecting step for selecting a search by the before/after search executing step, wherein the before/after search executing step searches the examination information in accordance with the selection by the before/after search selecting step.

10. An endoscope image filing method according to claim 3, the endoscope examination information recording step comprising:
- a log-in step for logging in; an examination schedule checking step for checking an examination schedule;
- a patient information registering step for registering patient information; an examination reserving step for inputting an examination reservation;
- an examination executing step for storing endoscope images obtained by an endoscope examination;
- an image selecting step for selecting an image to be referred to for creating an examination report among the endoscope images obtained by the examination executing step;
- a report creating step for creating an examination report; and
- an implementation information inputting step for inputting an examination-related implementation information.

11. An endoscope image filing method according to claim 3, the search condition inputting step comprising a list display step for searching examination information in accordance with an initial condition, for displaying a list of examination information and for storing the initial condition; and a GUI input waiting step for waiting an input through an input button displayed on a displayed screen.

12. An endoscope image filing system according to claim 5, the personal computer comprising:
the CPU, the ROM and the RAM functioning as the endoscope examination information search means, the before/after search setting means and the before/after search executing means;
the VRAM and a monitor connecting to the VRAM functioning as the examination information display means;
the hard disk functioning as the endoscope examination information recording means; and
a keyboard connected to the keyboard interface portion and a mouse connected to the mouse interface portion functioning as the search condition input means.

13. The endoscope image filing system according to claim 5,
wherein the personal computer is connected to the endoscope device through the communication interface portion and the video circuit;
wherein the communication interface portion exchanges different kinds of data with the endoscope device in the RS232C format;
wherein an image signal is input from the endoscope device to the video circuit;
wherein the A/D converting portion MD converts the image signal input to the video circuit; and
wherein the image memory temporally stores image data output from the A/D converting portion.

14. An endoscope image filing system according to claim 7, the personal computer comprising:
the CPU, the ROM and the RAM functioning as the endoscope examination information search means, the before/after search setting means and the before/after search executing means; the VRAM and a monitor connecting to the VRAM functioning as the examination information display means;
the hard disk functioning as the endoscope examination information recording means; and
a keyboard connected to the keyboard interface portion and a mouse connected to the mouse interface portion functioning as the search condition input means and the before/after search selecting means.

15. The endoscope image filing system according to claim 7,
wherein the personal computer is connected to the endoscope device through the communication interface portion and the video circuit;
wherein the communication interface portion exchanges different kinds of data with the endoscope device in the RS232C format;
wherein an image signal is input from the endo scope device to the video circuit;
wherein the A/D converting portion A/D converts the image signal input to the video circuit; and
wherein the image memory temporally stores image data output from the A/D converting portion.

16. An endoscope image filing method according to claim 9, causing the image filing device to execute:
the endoscope examination information search step for searching the examination information recorded by the endoscope examination information recording step in accordance with the search condition input from the search condition input step;
the examination information display step for searching the examination information, which is the search result;
the before/after search selecting step for selecting a search by the before/after search executing step based on the displayed search result;
the before/after search setting step for changing a search range under the predetermined condition based on the select result by the before/after search selecting step;
the before/after search executing step for searching the examination information recorded by the endoscope examination information recording step based on the changed search range and in accordance with the selection by the before/after search selecting step; and
the examination information display step for displaying the search information, that is the search result.

17. An endoscope image filing method according to claim 11, wherein the endoscope examination information search step performs processing in accordance with an input button input by the GUI input waiting step in the search condition input step.

18. An endoscope image filing method according to claim 17, wherein the input button is a date before/after search button for searching date information as the search condition; and wherein the endoscope examination information search step searches endoscope examination information in accordance with date information input by the date before/after search button.

19. An endoscope image filing method according to claim 17, wherein the input button is an end button for finishing a search; and wherein the endoscope examination information search step finishes the search in accordance with end information input by the end button.

20. An endoscope image filing method according to claim 18, wherein the before/after search setting step obtains date information searched by the endoscope examination information searching step and sets the obtained date information.

21. An endoscope image filing method according to claim 20, wherein the before/after search executing step searches corresponding endoscope examination information based on the date information set by the before/after search setting step; and wherein the examination information display step displays the searched endoscope examination information.

* * * * *